United States Patent [19]
Nimni

[11] Patent Number: 5,935,994
[45] Date of Patent: Aug. 10, 1999

[54] NUTRITIONALLY BALANCED DERMAL COMPOSITION AND METHOD

[76] Inventor: Marcel E. Nimni, 2800 Neilson Way, Apt. 908, Santa Monica, Calif. 90405

[21] Appl. No.: 09/087,594

[22] Filed: May 29, 1998

[51] Int. Cl.⁶ .................. A61K 31/355; A61K 31/34; A61K 31/195

[52] U.S. Cl. .................. 514/458; 514/474; 514/561; 514/562

[58] Field of Search .................... 514/561, 562, 514/474, 458

[56] References Cited

U.S. PATENT DOCUMENTS 4,201,235 5/1980 Ciavetta ........................ 132/7

FOREIGN PATENT DOCUMENTS 2617919   11/1976  Germany .
09030964 A2  2/1997  Japan .
97-US5114  3/1997  WIPO .

*Primary Examiner*—Raymond Henley, III
*Attorney, Agent, or Firm*—Oppenheimer Wolff & Donnelly LLP

[57] ABSTRACT

A composition and method for enhancing the appearance of the skin, the composition containing a mixture of essential amino acids, a penetrant, a neucleotide, vitamin C and vitamin E.

6 Claims, No Drawings

NUTRITIONALLY BALANCED DERMAL COMPOSITION AND METHOD

FIELD OF THE INVENTION

This invention relates to enhancing the well being and appearance of the skin by diffusing skin nutrients across the epidermal barrier of the skin.

BACKGROUND OF THE INVENTION

The application of substances to the skin with the objective of enhancing its appearance has been practiced for thousands of years. Such substances are usually applied in liquid or semisolid forms and include a large number of materials of plant, animal or synthetic origin.

Anatomically the skin can be described as a stratified organ with three distinct tissue layers: the epidermis, the dermis and the subcutaneous fat layer.

The epidermis, the outermost skin layer is comprised of stratified squamous epithelial cells. On the surface of this layer, the flattened remnants of the dividing cells which originate from the lower basal area accumulate forming a relatively thin coating which serves as a barrier between the integument and the environment. This outermost area which is about $10\mu$ in thickness, is known as the stratum corneum and is very rich in keratin, a protein that contributes to the cytoskeleton of the epidermal cells. The stratum corneum has the capacity to retain water to a much greater extent than other keratinized tissues such as nails and skin. This water retention is temporary, since water readily evaporates due to the physical location, in contact with the external environment, and body temperature. The stratum corneum serves as a protective physical and chemical barrier for the body preventing the penetration of most substances via the skin.

Dry, rough and pigmented skin is a common occurrence associated with the aging process. As skin ages, it thins and hygroscopic substances decrease reducing the ability of the skin to retain water. Hormonal changes that accompany aging result in lower sebum output and therefore lowered skin lubrication. In addition, keratin cross-linking induced by long term exposure to UV radiation causes skin to harden.

Water diffuses rapidly to the keratin layer from the lower skin layers, at a rate about 50–100 times faster than it is lost by evaporation. Water movement through the keratin layer is rather slow due to the intercellular lipid component that surrounds the keratinocytes (where the keratinocytes can be considered the bricks and lipids the mortar).

In the skin there are natural water retaining, or moisturizing factors which can be easily removed by excessive washing, leading to a dry skin condition.

Substances applied on the skin can alter the skin surface if their penetration is blocked by the stratum corneum by forming a cuticle or film. This film can act as an antimicrobial if the substance applied has antimicrobial properties, can protect against sun damage if it contains a sunscreen or can have cleansing effects if it contains surfactants.

Films can display different degrees of occlusiveness providing a moisturizing effect, not due to their water content, which as mentioned would rapidly evaporate, but by preventing the loss of water from the underlying skin.

The dry stratum corneum therefore becomes hydrated as the water is delayed in evaporating, and this increased moisture results in the skin feeling softer and attaining a transient smoother appearance. Since such barriers are hydrophobic in nature, they tend to generate an oily or shiny appearance and therefore can only be used in moderation and combined with hydrophilic substances, which by definition will restore water loss causing the skin to regain its original appearance.

Because of the natural protective function of the skin most substances are precluded from penetrating across the stratum corneum. However, this protective effect also precludes the penetration of macromolecules such as collagen, elastin, glycosaminoglycans, and other desirable substances which are lost from the underlying dermis during the process of aging. Thus, the application of such substances to the skin in the form of creams or ointments becomes a futile effort, since they cannot penetrate and become incorporated into the tissue. At the best they will generate a partially occlusive coating that will alter the natural appearance of the skin.

SUMMARY OF THE INVENTION

The present invention provides for a method of penetrating the epidermis of the skin with a nutritionally balanced composition. The present invention also provides a formulation which contains essential nutrients, modulating factors, stimulators of the cellular activities of the epidermis and the dermis and a penetration enhancer which allows these molecules to enter the skin. The nutritionally balanced formulation of the present invention include: (a) essential amino acids in a ratio which is generally the same as their concentration in body fluids; (b) a lipid soluble form of vitamin C such as vitamin C palmitate; (c) stimulators of cellular biosynthetic activity; nucleic acids (purines and pyrimidines derived from DNA and RNA); and (d) vitamin E as an antioxidant and stabilizer. These ingredients are present in a balanced formulation tested experimentally to be optimal for the activity of fibroblasts and keratinocytes. By being able to deliver such nutrients to the replicating keratinocytes located at the base of the epidermis and to the fibroblasts of the dermis that synthesize macromolecules such as collagen, elastin and glycosaminoglycans, we can restore the youthful physico-chemical character of the skin. During the process of aging, the dermis becomes thinner and less hydrated due to the loss of such essential structural macromolecules. This gives rise to a vicious circle of events, which continues to impair the proper nutrition of the declining cell population. Optimizing cell nutrition restores the function and biosynthetic and reproductive capacity of such cells.

Since one of the critical macromolecules of the skin is collagen and since the collagen content of the skin declines with age it is important to evaluate modalities to enhance its synthesis. Vitamin C is a cofactor for the synthesis of collagen because it participates in an essential step of the biosynthetic process, namely the hydroxylation of proline to hydroxyproline, a key structural amino acid contributing to the helical configuration of the collagen molecule. Our investigations have confirmed this role of Vitamin C and in addition have established that a lipid soluble form of Vitamin C such as Vitamin C palmitate is more effective as a promoter of collagen synthesis than the normally used Vitamin C (ascorbic acid). One experiment showing the difference in the two forms of Vitamin C on the synthesis of collagen is presented in the graph below. These studies were done using human skin derived fibroblasts grown in tissue culture medium containing various levels of the two forms of Vitamin C, expressed in $\mu M$. It is clearly evident from the graph below that Vitamin C palmitate and other lipid soluble forms of Vitamin C are more effective in stimulating collagen syntheses especially at low concentrations, such as may be delivered to tissues. In addition to being a more potent promoter of collagen synthesis, lipid soluble forms of Vitamin C are not as readily oxidized in air as is Vitamin C. Most importantly, due to their solubility in lipids, this form of Vitamin C is more readily transported across the dermal-epithelial barrier, which coupled with the penetration enhancer in our formulation allows the Vitamin C to reach the fibroblasts of the dermis where it stimulates collagen synthesis.

As is apparent from the foregoing, the present invention provides a method for administering transdermally, in a topically pharmaceutical carrier such as a cream and/or lotion base, a series of nutrients essential for the nutrition of the cells of the epidermis and the dermis. Such nutrients will stimulate these cells to produce larger amounts of the components of the extracellular matrix such as collagen, elastin, glycosaminoglycans and other tissue specific macromolecules which normally decline with increasing age. The nutrients provided include a readily transportable and stable form of vitamin C, ascorbic acid palmitate; 10 essential amino acids required by human cells in a proportion which resembles their concentration in body fluids; the constituent bases of DNA and RNA and the antioxidant vitamin E (e.g. vitamin E linoleate) which prevents the destructive effect of free radicals which would inhibit cellular activity and stabilize the connective tissue network. In addition a sufficient amount of an organic penetrant is added to facilitate the transport of the above mentioned nutrients and stabilizers across the epidermal barrier.

Such organic penetrants include lower alkyl diols, $C_{10}$–$C_{20}$ fatty acids and esters thereof, and $C_4$–$C_{20}$ aliphatic alcohols. Exemplary of such penetrants are propylene glycol, oleic acid, butyl alcohol and, preferably, benzyl alcohol. Generally speaking, the amount of penetrant will vary between about 0.5 wt. % and about 10 wt. %.

The amount of vitamin C will vary from about 0.5 wt. % to about 5 wt. %. The amount of vitamin E will be present in an amount of from about 0.5 wt. % to about 5 wt. % and the amount of nucleotide present will be from 0% to 0.01 wt. % to as high as 1 or 2 wt. %. The amount of the mixtures of essential amino acid present in the composition will be between about 0.01 wt. % and about 5 wt. %. The mixture itself may be constituted as follows:

| ACID | AMOUNT (WT. %) MIXTURE OF AMINO ACIDS |
|---|---|
| Isoleucine | 5–20 |
| Leucine | 5–20 |
| Lysine | 10–25 |
| Methionine | 2–5 |
| Phenylalanine | 5–20 |
| Threonine | 5–25 |
| Tryptophan | 5–20 |
| Valine | 10–25 |
| Histidine | 5–20 |
| Arginine | 5–20 |

DETAILED DESCRIPTION OF THE PREFERRED EMBODIMENTS

The main approach used to treat dry, weathered or aged skin involves raising the moisture content of the stratum corneum. Most methods currently employed rely on the transient blocking of the water loss using one sort of a barrier or other (occlusive agents, oils, etc). The water retaining components of the skin, particularly of the dermis, which acts as reservoirs which supply water to the epidermis, are well characterized and consist of specialized protein and sugar containing compounds called proteoglycans and glycosaminoglycans. Since these decline with age, it is desirable to stimulate the cells of the skin responsible for their biosynthesis to increase their metabolic activities leading to the formation of such macromolecules.

This is done by delivering transdermally a specially formulated balanced mixture of compounds which include certain of the essential amino acids, vitamin E, vitamin C and, optionally, a nucleotide.

EXAMPLE 1

A moisturizing cream containing the following active ingredients in weight percent:

| | |
|---|---|
| Essential amino acid mixture | .05% |
| Nucleotides derived from yeast RNA | 0.1% |
| Tocopherol palmitate | 10% |
| Vitamin C palmitate | 1.0% |

All of the above are mixed in a topical pharmaceutical carrier containing: Water, propylene glycol, carbopol, octyl palmitate, silicone fluid, cetearyl alcohol, trietanolamine, non-sensitizing preservatives. This is prepared using standard procedures, and the individual active ingredients are added sequentially. To the final mixture benzyl alcohol is added to a final concentration of 1%. Water and oil phases are heated separately to 70° C., blended and cooled with normal mixing. The final moisturizing cream has the following ingredients in weight percent:

| | % w/w |
|---|---|
| Water - | q.s. to 100 |
| Propylene glycol - | 2 |
| Carbopol 940 - | 1 |
| Dryflo PC (surface coated starch polymer, National Starch) - | .5 |
| Tocopherol palmitate (Vit. E) - | 10 |
| Ascorbyl palmitate (Vit. C) - | 1 |
| Octyl palmitate - | 1 |
| Isopropyl palmitate - | 2 |
| Silicone fluid (200 cs) - | 2 |
| Arlacel 165 (glyceryl stearate and PEG 100 stearate) - | 2 |
| Cetearyl alcohol - | 1 |
| Stearic acid - | .5 |
| Triethanolamine - | .25 |
| Benzyl alcohol - | 2 |
| Capric/caprylic triglyceride (Miglyol 812) - | 2 |
| Capric/caprylic stearyl triglyceride (Softisan 378) - | .5 |
| Natural lavender/chamomile oils (for fragrance) - | .2 |
| Methyl paraben - | .2 (preservative) |
| Propyl paraben - | .05 (preservative) |
| Diazolidinyl urea (Germall 2) - | .2 (preservative) |
| RNA/DNA powder - | .1 |
| Essential amino acids - | .05 |

The composition of the essential amino acids in the above formulation is as follows:

| | |
|---|---|
| Isoleucine | 15mg |
| Leucine | 20mg |
| Lysine | 26mg |
| Methionine | 6mg |
| Phenylalanine | 15mg |
| Threonine | 22mg |
| Tryptophan | 14mg |
| Valine | 30mg |
| Histidine | 15mg |
| Arginine | 20mg |

What is claimed is:

1. A composition for topical application consisting essentially of (a) from about 0.01 wt. percent to about 5 wt. percent of a mixture of amino acids consisting essentially of from about 15 parts by weight of isoleucine, from about 20 parts by weight of leucine, from about 26 parts by weight of lysine, from about 6 parts by weight of methionine, from about 15 parts by weight of phenylalanine, from about 22 parts by weight of threonine, from about 14 parts by weight of tryptophan, from about 30 parts by weight of valine, from about 15 parts by weight of histidine and from about 20 parts by weight of arginine, (b) from about 0.5 wt. percent to about 10 wt. percent of an organic skin penetrant, (c) from about 0.5 wt. percent to about 5 wt. percent of lipid soluble vitamin C, (d) from about 0.5 wt. percent to about 10 wt. percent of vitamin E, and (e) a topical pharmaceutical carrier.

2. The composition of claim 1 wherein the lipid soluble vitamin C is vitamin C palmitate.

3. The composition of claim 1 wherein the penetrant is benzyl alcohol.

4. A method of enhancing the appearance of the skin which comprises applying to the skin a topical formulation consisting essentially of (a) from about 0.01 wt. percent to about 5 wt. percent of a mixture of amino acids consisting essentially of from about 15 parts by weight of isoleucine, from about 20 parts by weight of leucine, from about 26 parts by weight of lysine, from about 6 parts by weight of methionine, from about 15 parts by weight of phenylalanine, from about 22 parts by weight of threonine, from about 14 parts by weight of tryptophan, from about 30 parts by weight of valine, from about 15 parts by weight of histidine and from about 20 parts by weight of arginine, (b) from about 0.5 wt. percent to about 10 wt. percent of an organic skin penetrant, (c) from about 0.5 wt. percent to about 5 wt. percent of lipid soluble vitamin C, (d) from about 0.5 wt. percent to about 10 wt. percent of vitamin E, and (e) a topical pharmaceutical carrier.

5. The method of claim 4 wherein the lipid soluble vitamin C is vitamin C palmitate.

6. The method of claim 4 wherein the penetrant is benzyl alcohol.

\* \* \* \* \*